(12) United States Patent
Graessle et al.

(10) Patent No.: US 7,171,256 B1
(45) Date of Patent: Jan. 30, 2007

(54) BREAST MAGNETIC RESONACE IMAGING SYSTEM WITH CURVED BREAST PADDLES

(75) Inventors: David Graessle, Dublin, OH (US); Alan L. Oslan, Bedford, MA (US); Stephen D. Venditti, Newton, MA (US); Gunther Becht, Somerville, MA (US); Mathew A. Hass, Andover, MA (US)

(73) Assignee: Aurora Imaging Technology, Inc., North Andover, MA (US)

( * ) Notice: Subject to any disclaimer, the term of this patent is extended or adjusted under 35 U.S.C. 154(b) by 556 days.

(21) Appl. No.: 10/302,734

(22) Filed: Nov. 21, 2002

Related U.S. Application Data

(60) Provisional application No. 60/332,563, filed on Nov. 21, 2001.

(51) Int. Cl.
*A61B 6/00* (2006.01)
(52) U.S. Cl. ............... 600/427; 600/407; 600/429; 600/439; 378/37; 128/915; 128/916
(58) Field of Classification Search ............... 600/427, 600/439, 415, 407, 429, 562; 378/37, 204; 128/897, 915–6; 607/101–2, 98; 604/116
See application file for complete search history.

(56) References Cited

U.S. PATENT DOCUMENTS

| | | | |
|---|---|---|---|
| 4,981,142 A | * | 1/1991 | Dachman ............... 600/562 |
| 5,078,142 A | | 1/1992 | Siczek et al. |
| 5,289,520 A | | 2/1994 | Pellegrino et al. |
| 5,386,447 A | | 1/1995 | Siczek |

(Continued)

FOREIGN PATENT DOCUMENTS

DE 19626286 1/1998

OTHER PUBLICATIONS deSouza et al., "MR-Guided Biopsy of the Breast After Lumpectomy and Radiation Therapy Using Two Methods of Immobilization in the Lateral Decubitus Position, " JMRI, pp. 525-528 (Sep./Oct. 1995).
Doler et al., "Stereotaxic Add-on Device for MR-guided Biopsy of Breast Lesions," pp. 863-864 (Sep. 1996).

(Continued)

Primary Examiner—Brian L. Casler
Assistant Examiner—Baisakhi Roy
(74) Attorney, Agent, or Firm—Fish & Richardson P.C.

(57) ABSTRACT

A patient support table for breast MRI systems, the table including a base configured to slide into and out of the bore of an MRI system; a patient support member attached to the base and having a top surface shaped to support a patient in a prone position; two breast openings in the patient support member, the breast openings being sized and positioned to permit the patient's breasts to extend downward beneath the patient support member, at least a pair of breast immobilization paddles, one on each side of a breast opening, the immobilization paddles comprising a grid of breast contact elements that contact the breast while providing a plurality of openings through which a surgical tool may be inserted into the breast, and the paddles having a convex curvature along the Z direction (head to toe) so that the breast contacting surface of each paddle is further from the Y-axis center line of the breast opening midway along the Z extent of the paddle than at the Z extremities of the paddle.

9 Claims, 11 Drawing Sheets

U.S. PATENT DOCUMENTS

| | | | |
|---|---|---|---|
| 5,409,497 A | 4/1995 | Siczek et al. | |
| 5,569,266 A | 10/1996 | Siczek | |
| 5,590,655 A | 1/1997 | Hussman | |
| 5,678,549 A | 10/1997 | Heywang-Koebrunner et al. | |
| 5,706,812 A | 1/1998 | Strenk et al. | |
| 5,855,554 A | 1/1999 | Schneider et al. | |
| 5,913,863 A | 6/1999 | Fischer et al. | |
| 6,254,538 B1 | 7/2001 | Downey et al. | |
| 6,423,076 B1 | 7/2002 | Cardwell et al. | |
| 6,470,217 B1 * | 10/2002 | Fenn et al. | 607/101 |
| 6,876,879 B2 * | 4/2005 | Dines et al. | 600/427 |
| 2002/0156365 A1 | 10/2002 | Tsekos | |
| 2003/0007598 A1 | 1/2003 | Wang et al. | |

OTHER PUBLICATIONS

Fischer et al., "Magnetic Resonance Guidance Localization and Biopsy of Suspicious Breast Lesions," Topics in Magnetic Resonance Imaging, 9,(1):44-59 (1998).

Heywang-Kobrunner et al., "MR-Guided Percutaneous Vaccum Assisted Biopsy of Enhancing Breast Lesions," Electromedica, 67(2):67-45 (1999).

Heywang-Kobrunner et al., "Prototype Breast Coil for MR-Guided Needle Localization," Journal of Computer Assisted Tomography, 18(6):876-881 (1994).

Hussman et al., "MR Mammographic Localization-Work in Progress," Radiology, 189(3):915-917 (1993).

Schnall et al., "MR Guided Biopsy of the Breast," Breast Imaging, MRI Clinics of North America, 2(4):585-589 (Nov. 1994).

* cited by examiner

BREAST MAGNETIC RESONACE IMAGING SYSTEM WITH CURVED BREAST PADDLES

CROSS-REFERENCE TO RELATED APPLICATIONS

This application claims priority to U.S. Provisional Application Ser. No. 60/332,563, filed on Nov. 21, 2001 (hereby incorporated by reference). This application incorporates by reference the disclosure of U.S. patent application Ser. No. 10/301,805, filed Nov. 21, 2002, entitled "Patient Support Table for Breast MRI System".

BACKGROUND

The invention relates to magnetic resonance imaging (MRI) systems, particularly MRI systems for imaging breasts.

MRI systems typically employ a main magnet that produces a static magnetic field and gradient coils that superimpose spatially varying magnetic fields on top of the static field. The gradient coils are typically formed on a cylindrical insert that fits within the bore of the main magnet. Inside of the gradient coil insert there are RF transmitting and RF receiving coils (sometimes the same coil). The RF transmitting coil excites the molecules of the anatomy being imaged, and the RF receiving coil detects the response of the molecules.

MRI images can be used to guide biopsy and surgical tools. The anatomy of interest is imaged with one or more reference ("fiducial") markers appearing in the image (or series of images). The surgical tool is installed in a known relationship to the reference markers (e.g., in a rotatable tool holder), and the tool is positioned so that upon insertion it will reach the lesion or other target found in the image (e.g., the tool holder is adjusted so that the target is at the center of rotation of the holder). Knowing the locations of the reference marker and the lesion makes IT possible to determine the position and orientation that the tool should be in for it to reach the target when inserted.

Often, the biopsy or surgical procedure is done after the patient is withdrawn from the MRI system, but the anatomy of interest is typically held stationary between the time that the images are taken and the surgery is completed.

This technique has been applied to some degree in biopsy of breast lesions. For example, in Schneider U.S. Pat. No. 5,855,554, MRI-transparent breast stabilization plates hold the breasts stationary, and reference markers built into the plates provide information for orienting the biopsy tool.

SUMMARY

In general, the invention features a patient support table for breast MRI systems, the table comprising a base configured to slide into and out of the bore of an MRI system; a patient support member attached to the base and having a top surface shaped to support a patient in a prone position; two breast openings in the patient support member, the breast openings being sized and positioned to permit the patient's breasts to extend downward beneath the patient support member, at least a pair of breast immobilization paddles, one on each side of a breast opening, the immobilization paddles comprising a grid of breast contact elements that contact the breast while providing a plurality of openings through which a surgical tool may be inserted into the breast, and the paddles having a convex curvature along the Z direction (head to toe) so that the breast contacting surface of each paddle is further from the Y-axis center line of the breast opening midway along the Z extent of the paddle than at the Z extremities of the paddle.

In preferred implementations, one or more of the following may be incorporated. The convex curvature may be greatest at the edge of the paddles corresponding to the base of the breasts at the chest wall. The convex curvature may be progressively less at locations on the paddle further from the edge corresponding to the base of the breasts at the chest wall. The paddles may be substantially flat without curvature at the edge opposite the edge with curvature. The convex curvature at the edge corresponding to the base of the breast may have a radius of curvature of at least 50 mm (preferably at least 100 mm). The paddles may be further shaped so that at the paddle edge closest to the breast opening, and to the chest when a breast is immobilized by the paddles, the paddles are flared outwardly with a radius of curvature greater than about 10 mm (preferably greater than about 15 mm).

Other features and advantages will be apparent from the following detailed description and drawings.

DESCRIPTION OF DRAWINGS

FIG. 4A is a cross section view taken at 4A—4A in FIG. 4 showing the flare of the upper edge of the paddles.

DETAILED DESCRIPTION

Figure 1:
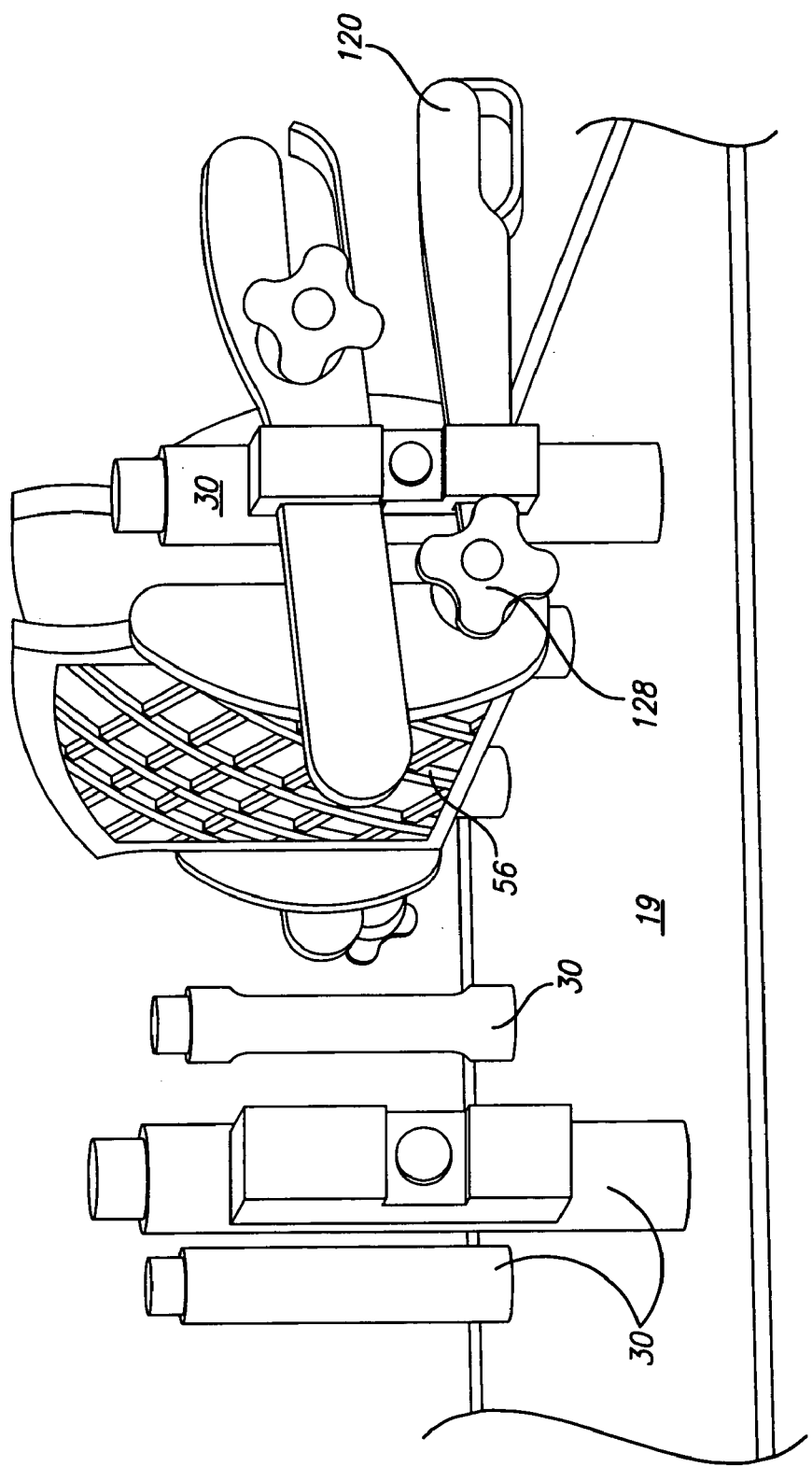
FIGS. 1–3 are perspective views (photographs) of the breast immobilization paddles and associated mechanisms of a preferred embodiment of the invention.

A description of the patient support table and the MRI system can be found in the disclosure of U.S. patent application Ser. No. 10/301,805, filed Nov. 21, 2002,. The surgical tool holder of the invention is installed in the vicinity of the breasts between the chest support member 44 and the base member 20.

FIGS. 1–4 show the five column shaped RF coil housings 30 that extend between the chest support member 44 and base plate 19, and one pair of breast immobilization paddles 56. Another pair is installed on the other side of the base plate. The columns 30 also serve to support the breast paddles and their adjustment mechanisms.

Figure 4:
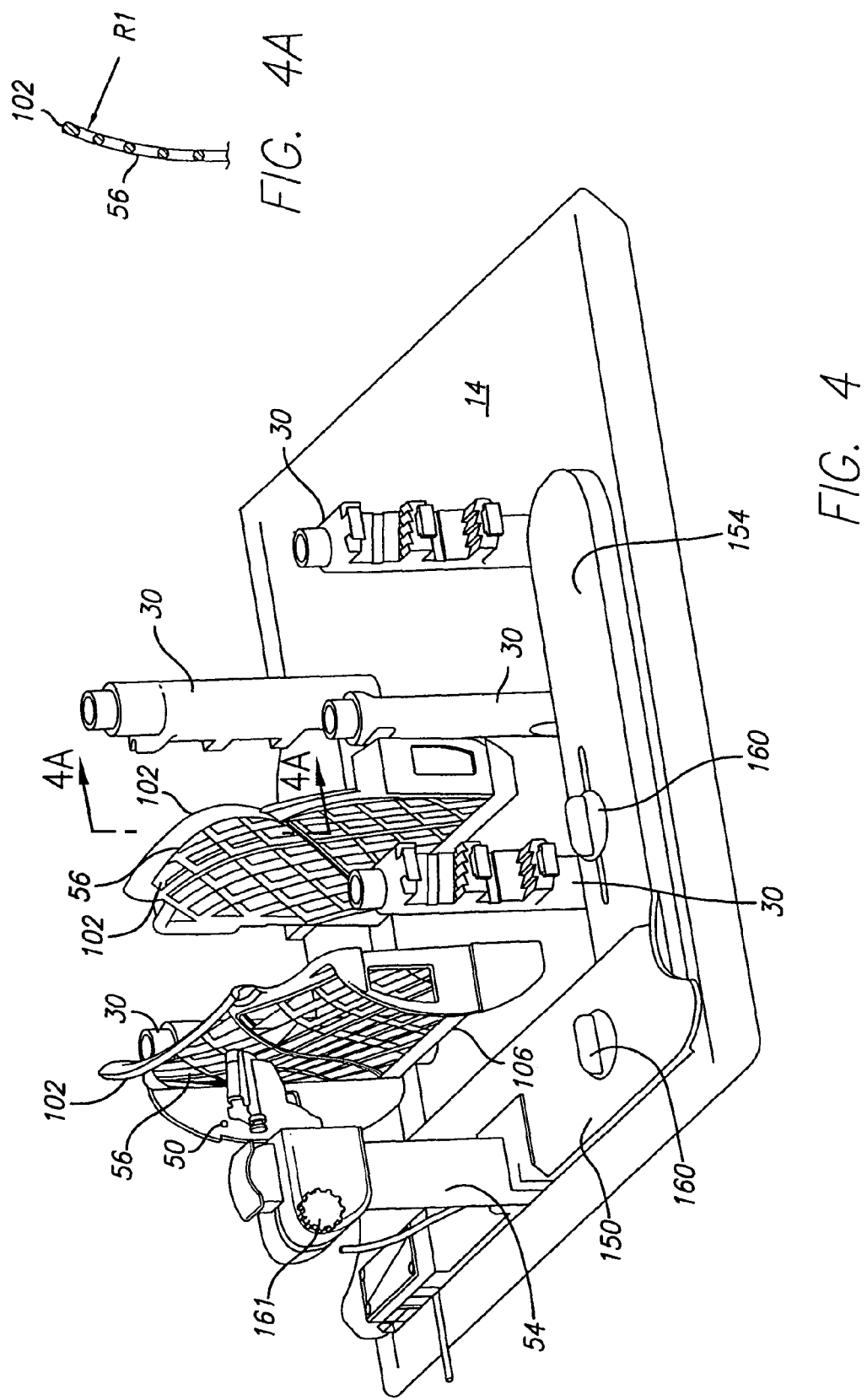
FIG. 4 is a perspective view of the same paddles and mechanisms.

The breast paddles have unique shapes designed to improve patient comfort, breast immobilization, and biopsy access. At their upper edges 102 (FIG. 4), which contact the chest wall on the left and right sides of each breast (extending nearly all of the way through the breast openings), the paddles are flared outwardly in the X direction, with a radius of curvature R1 of about 20 mm (FIG. 4A). The radius of curvature may be different than 20 mm, but it should be greater than 10 mm, and preferably greater than 15 mm. This shape has the advantages of greater comfort, and greater conformity with the breast so that this portion of the breast tissue is captured and immobilized. Openings 104 in the breast paddles extend close to the upper edge 102, so that a surgical tool may be inserted close to the chest wall.

Figure 5:
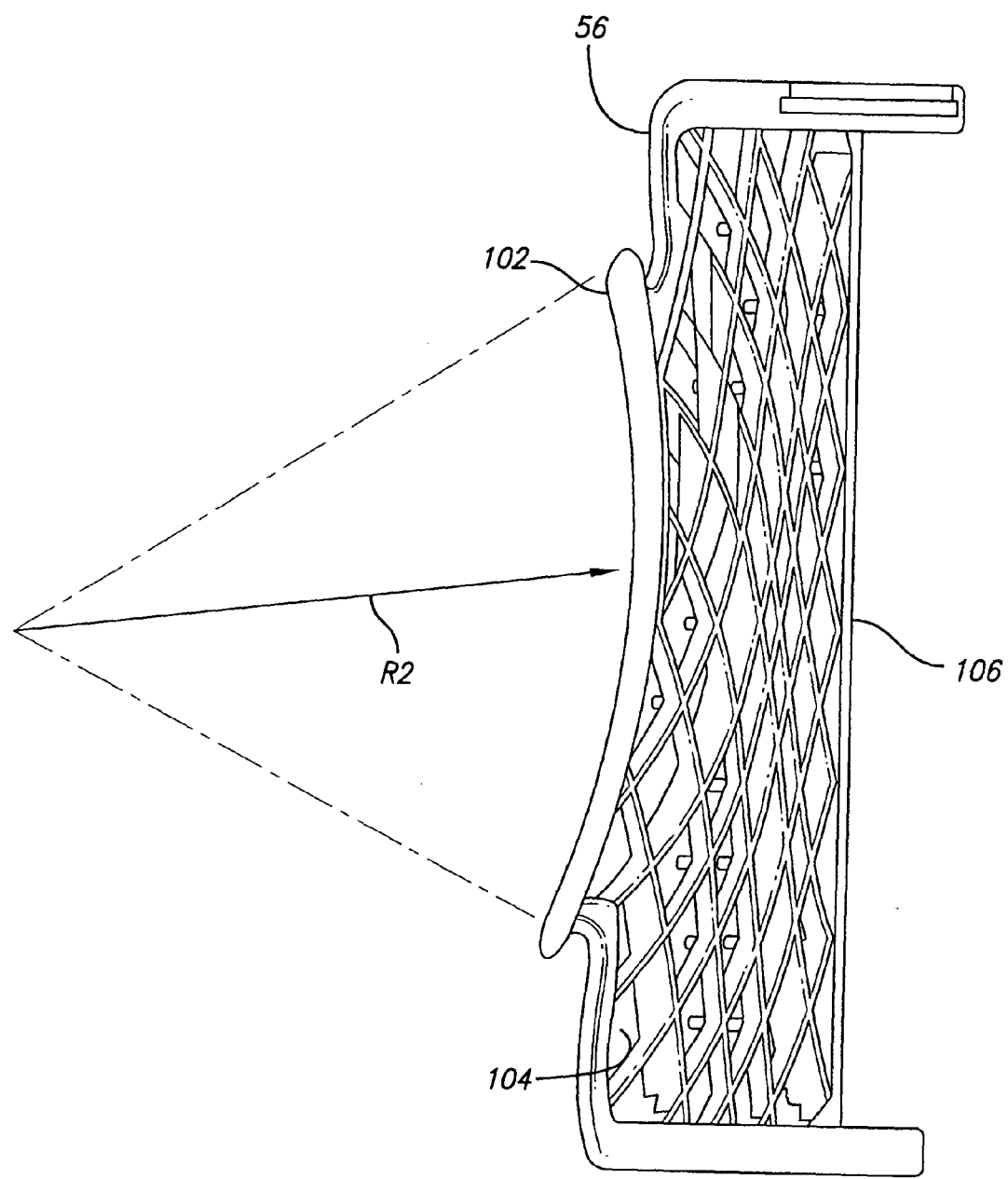
FIGS. 5–6 are views of a single breast paddle.

Another respect in which the paddles are shaped is the curvature of the upper edge along the Z direction (head to toe). This is best seen in FIG. 5. This curvature has a radius R2 of curvature of about 150 mm. Preferably the radius of curvature is greater than 50 mm, and more preferably greater than 100 mm. The curvature is designed to match the breast anatomy, while also permitting access by a surgical tool. The curvature is substantially the same as the curvature of the side of the breast opening through which it extends. Both paddles have a similar curvature at this upper edge. The curvature becomes progressively less until at the lower edge 106 of the paddle there is substantially no curvature, and the paddle is flat.

Figure 6:
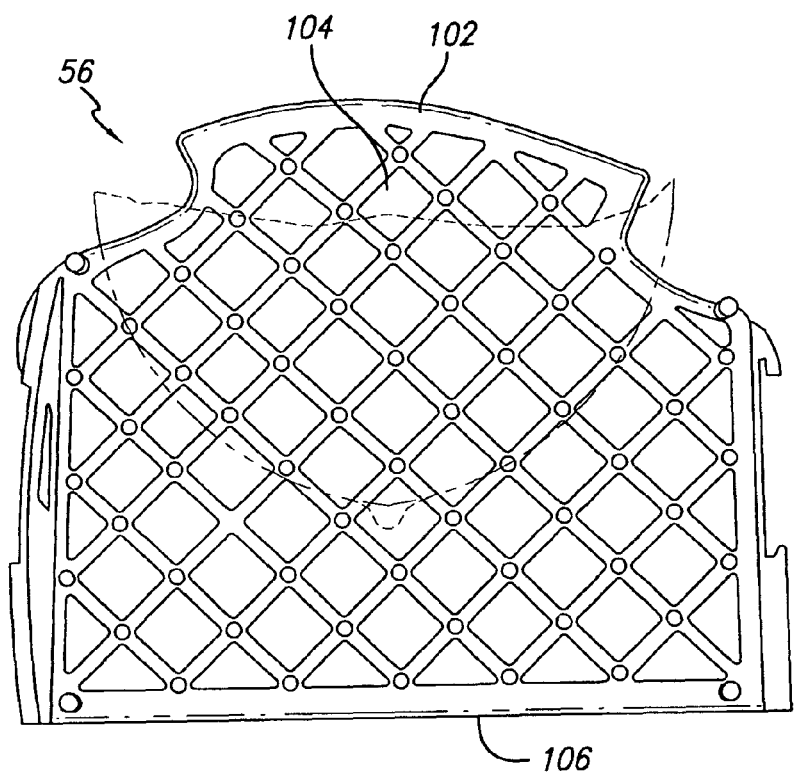

The grid elements extending across the extent of the paddles have several important features. Preferably they are oriented on the diagonal, as at this orientation they line up better with the periphery of the breast, as illustrated in FIG. 6. This means that along the periphery, nearly entire grid openings are spanned by the breast. Were the grid elements to extend vertically and horizontally, the breast periphery would be broken up between a greater number of grid elements, making it harder and less convenient for the surgeon to align the surgical tool for insertion to a lesion along the periphery. Although not necessary in the preferred embodiment disclosed herein, the diagonal orientation of the grid elements has the further advantage that by moving the tool holder only in either X or Y directions, without rotating it (as is possible in the preferred embodiment shown) it is possible to find an insertion path that avoids hitting the grid. That would not usually be true if the grids were oriented vertically and horizontally.

Figure 7:
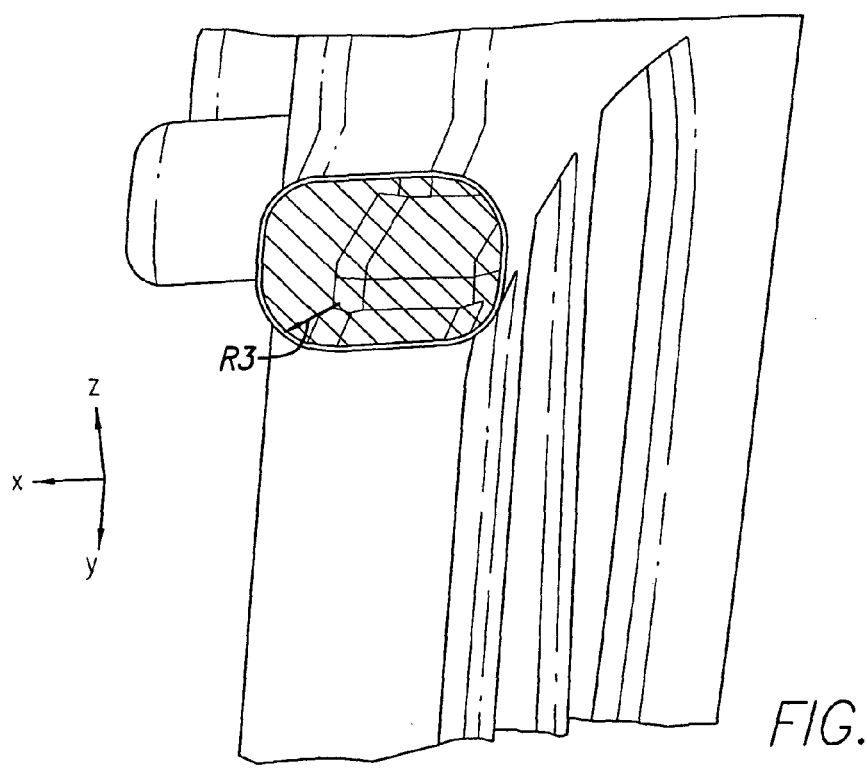
FIG. 7 is an enlarged cross section through a grid element of a breast paddle.

The cross sectional shape of the grid elements is preferably selected so that the edges that contact the breast tissue have a curvature with a radius of curvature R3 in the range of 0.5 to 5.0 mm, and preferably 1.0 to 3.0 mm. In FIG. 7, a cross section through one grid element is shown enlarged. The edge of the grid that contacts the breast tissue is to the right of the grid element, and it has corners each with a radius of curvature R3. This curvature tends to adhere better to the breast tissue, so that the skin is held taut between the grid elements. Preferably, the openings formed by the grid elements are in the range of 10 mm to 30 mm.

Some of the grid elements have differently shaped skin-contacting surfaces, with the intention that the different indentation shapes they produce will be visible in the MR image. Thus, the unique indentation pattern becomes a reference marker. This is particularly useful when a surgical tool is to be inserted manually without the benefit of the tool holder. The surgeon can locate the paddle opening closest to the lesion or target using the pattern of unique indentations.

Figure 8:
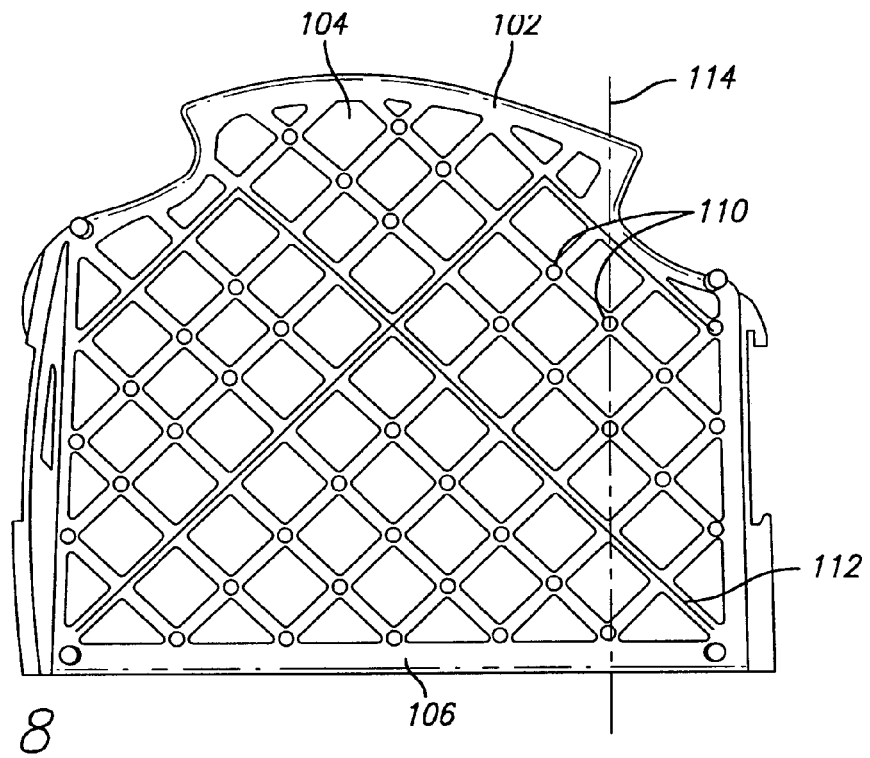
FIG. 8 is a view of a breast paddle with marker deformations shown.

Two types of indentations are shown in the embodiment. Ridges that extend along a grid element above the level of the other elements, and nubs that extend above the other elements at intersections of grid elements. FIG. 8 shows the same paddle as FIG. 6, with one possible layout of ridges 112 shown. Nubs 110 are placed at all grid intersections other than intersections with ridges 112. Different layouts of ridges and nubs can be used. The ridge layout shown in the figure was chosen so that when vertical slices oriented as shown at 114 are taken there would always tend to be two ridges that could possibly show up in the image.

The breast paddles can be adjusted in at least three ways to allow the paddles to conform to the patient's breast, and thereby hold it immobile with the skin taut. A paddle can be rotated about the Z axis, and translated left to right (X direction) at each end. By applying different amounts of translation at each end, it is possible, to some degree, to rotate the paddles about the Y axis. Thus, to some extent the paddles can be translated along the X axis, and rotated about the Z and Y axes.

Figure 2:
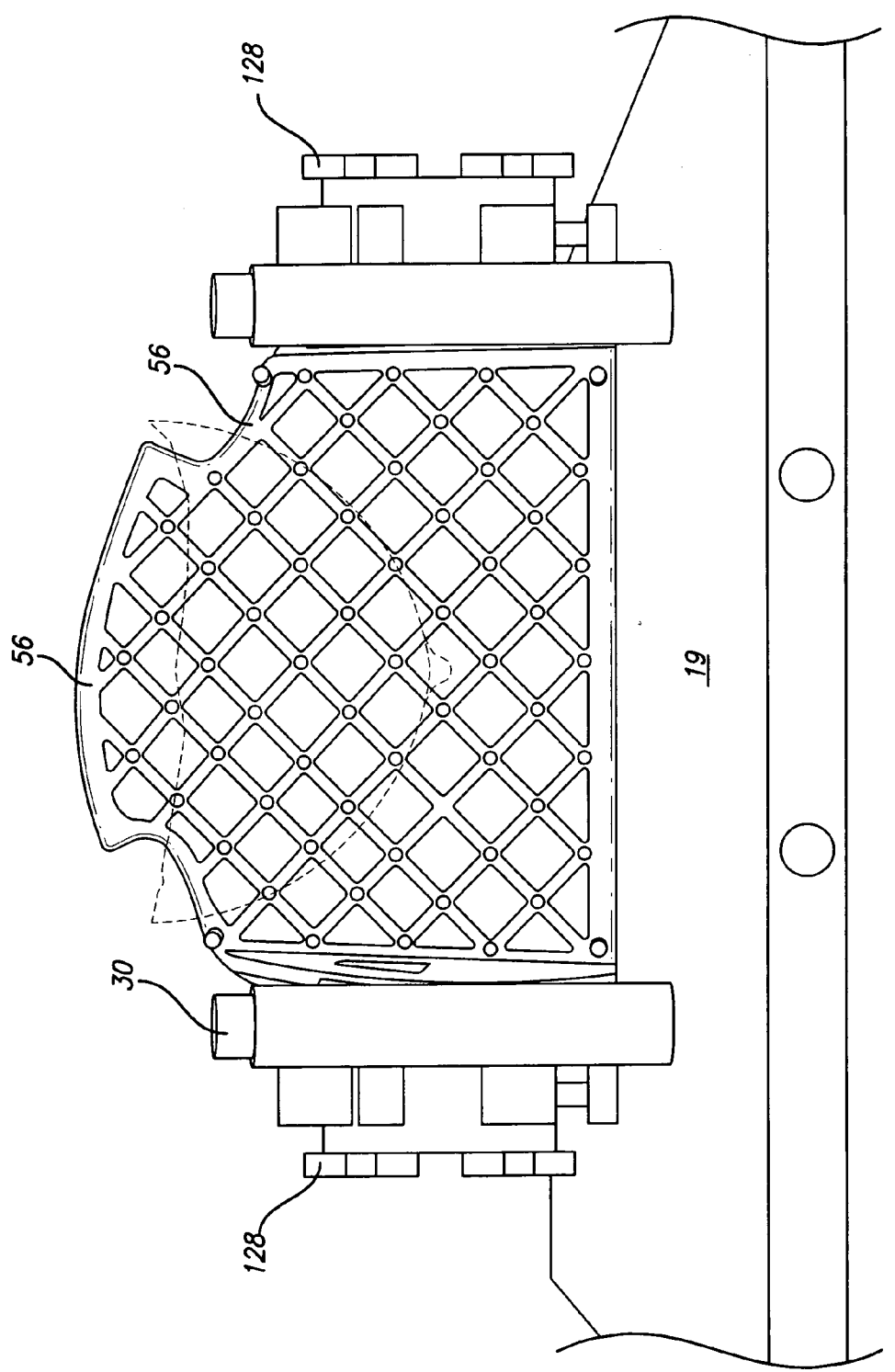
Figure 3:
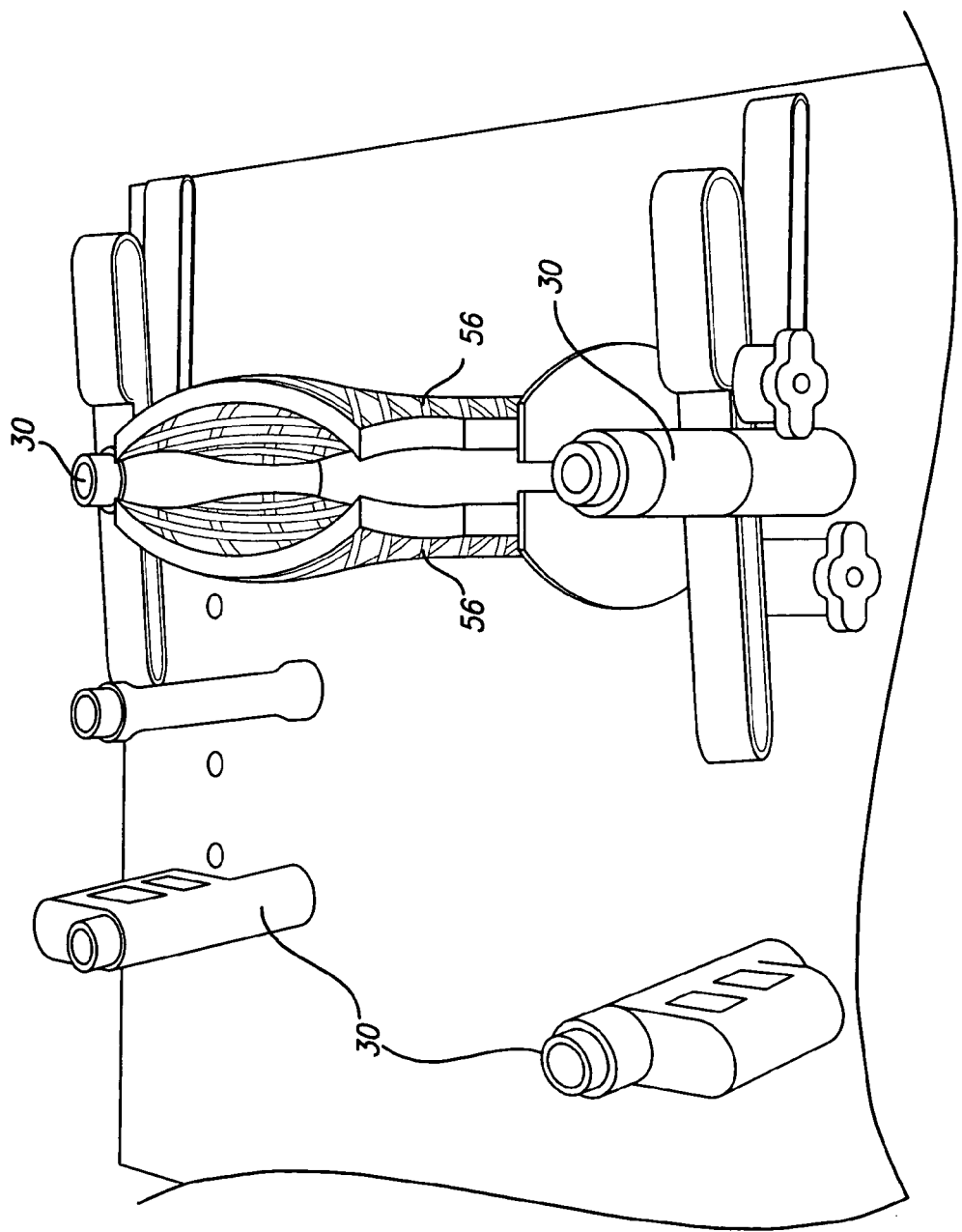
Figure 10:
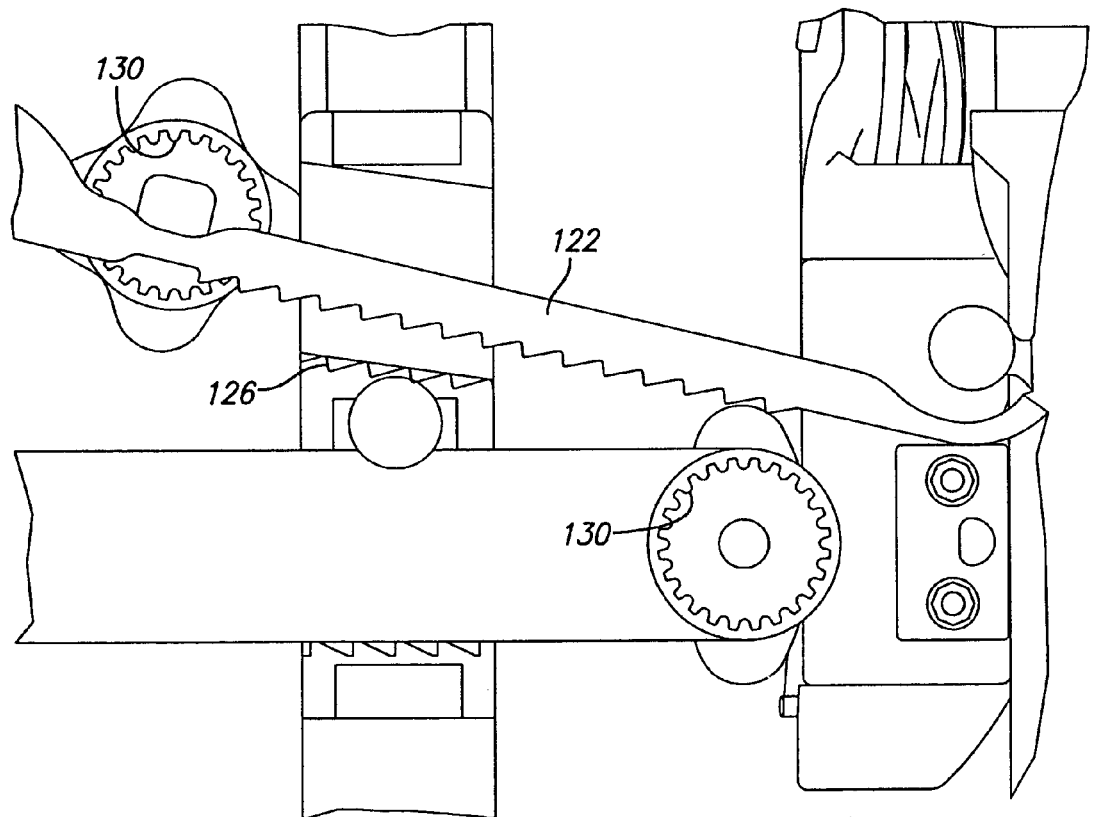
FIG. 10 is an enlargement of a portion of FIG. 9.
Figure 9:
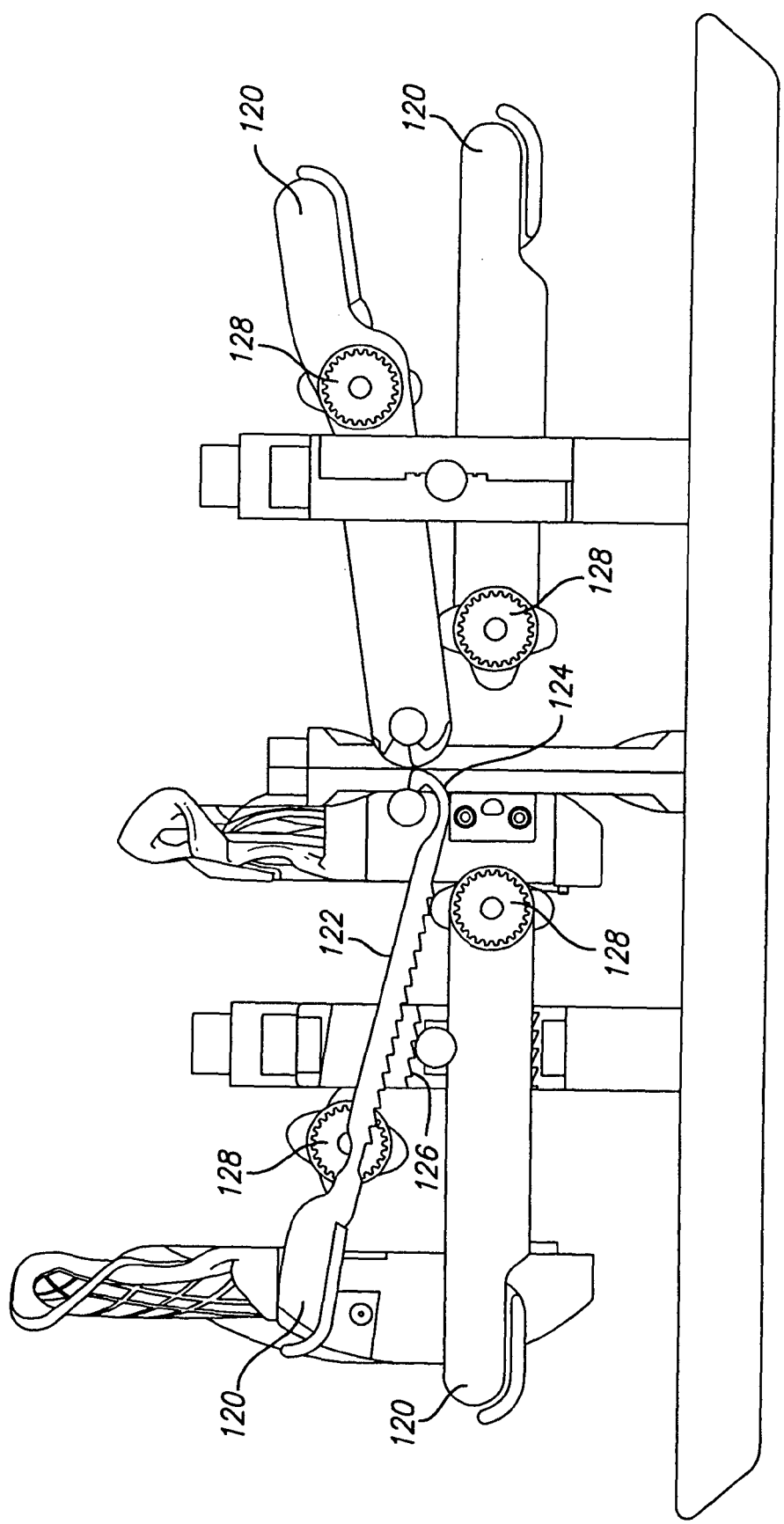
FIG. 9 is an elevation view, partially broken away, of the paddle adjustment mechanism.

The mechanisms for accomplishing the adjustment are shown in FIGS. 9–10, but various other types of mechanisms could be substituted, as the more important feature is that movement in a plurality of directions is made possible. In FIGS. 9–10 the mechanisms are partially disassembled. FIG. 10 is an enlargement of a portion of FIG. 9. In FIGS. 1–2 they are assembled.

To translate a paddle at one end, the handle 120 at that end is squeezed, which has the effect of lifting gear train 122, which flexes by bending at narrowed region 124. Lifting the gear train 122 disengages it from mating gear segment 126, to allow translation. By translating the two ends of a paddle differently, one can achieve both X translation and Y-axis rotation.

To rotate a paddle about the Z axis, knobs 128 at each end of the paddle must be pulled out in the Z direction. This has the effect of disengaging two sets of gear teeth 130 and permitting rotation of the paddle.

Figure 11:
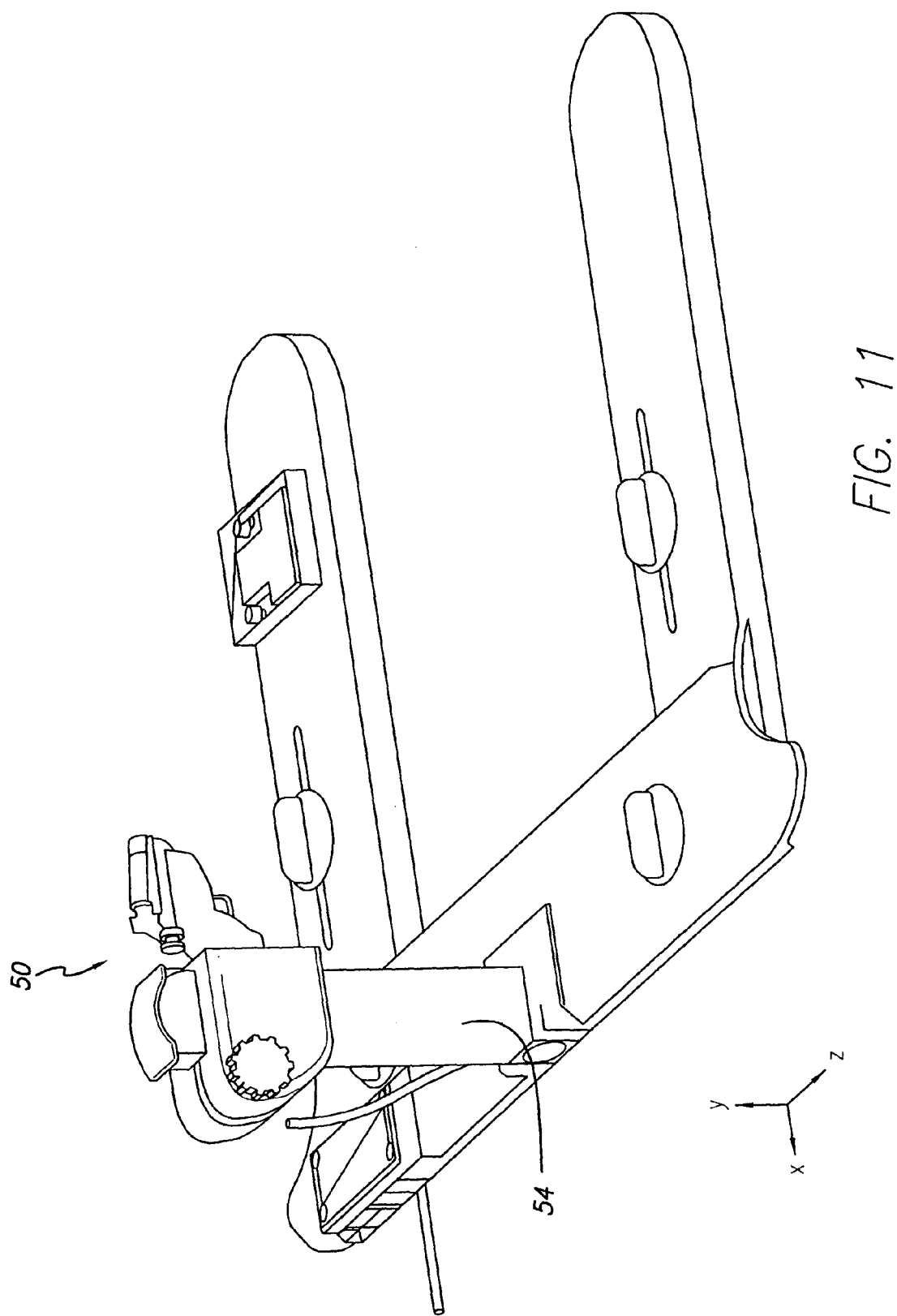
FIG. 11 is a perspective view of the surgical tool holder and adjustment elements.
Figure 12:
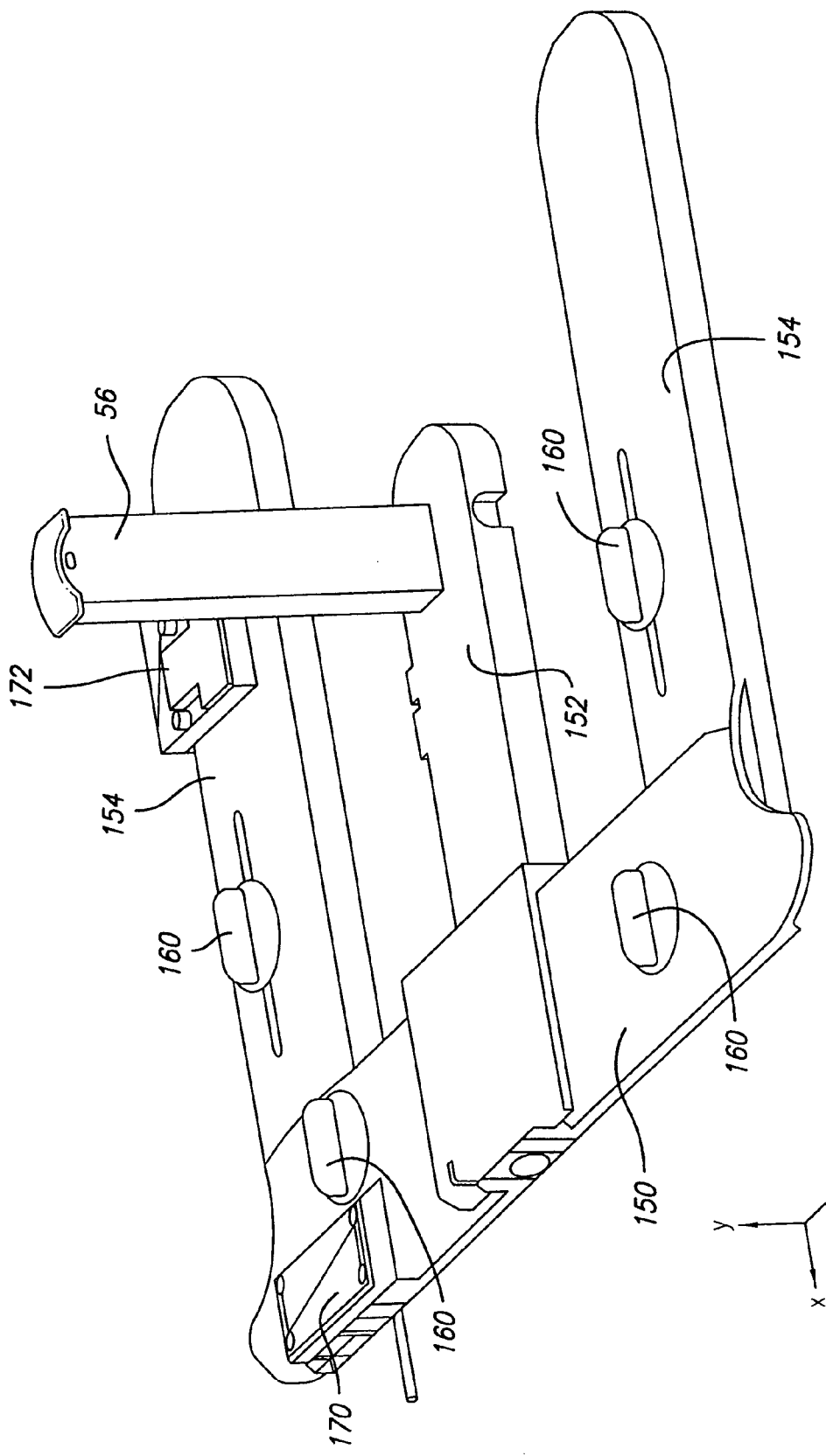
FIG. 12 is another view of the surgical tool holder adjustment elements.

The surgical tool holder 50 and supporting structure is shown in FIGS. 4, 11–12. FIGS. 11–12 show the tool holder installed in two different locations, one for medial access and the other for lateral access. The tool holder supports a surgical tool such as a biopsy needle (shown in FIGS. 11–12). The tool holder is supported on one of two posts 54, 56. Post 54 is used for lateral access, and post 56 for medial access. The posts are supported on adjustable support elements 150, 152, 154, which are secured, in turn, to base plate 19. Post 54 may be removed, and post 56 installed using an extension support element 152 when medial access is desired.

The tool holder may be translated in all three directions (X, Y, Z). Adjustment in the X and Z directions is accomplished by loosening the appropriate knob 160, and translating the appropriate support element 150, 154. The movement of the support elements is accurately measured by optical encoding sensors 170 (Z movement) and 172 (X movement). Adjustment in the Y direction is accomplished by loosing knob 161, and moving the holder up and down on post 54 (or 56). A third optical encoder on the post records the Y translation. At any chosen X, Y, Z location, the tool holder 50 can also be rotated about an X axis.

We have found that the optical encoders may incorporate light emitting diode (LED) elements, or other elements that contain small amounts of material that can distort MRI images.

We have been able to place the optical encoders far enough away (e.g., grater than 40 mm) from the anatomy being imaged (the breasts) that the distortion is reduced to an insignificant level. Other types of encoders could be used instead of optical encoders. All that is necessary is that the encoder observe some sort of indicia that moves by it, and put out a digital output based on observation of the moving indicia.

Figure 13:
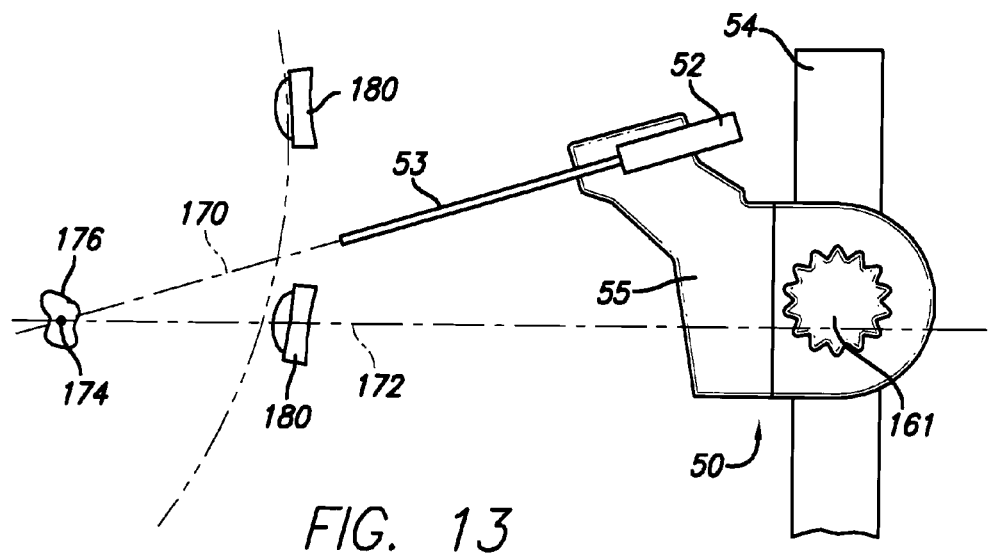
FIG. 13 is an elevation view of the surgical tool holder with tool installed.

Referring to FIG. 13, the tool 52 is oriented at an angle with respect to the X axis of rotation 172, and is positioned in the holder 50 so that the tool is inserted along an insertion direction 170 that intersects with the X axis of rotation 172 at target location 174. The goal of the MRI imaging, and adjustment of the tool holder, is to move the holder to a location at which the target location 174 is coincident with the lesion or anatomical target 176 found in the MRI image. The holder 50 has a base that is fixed to the post 54, and a rotatable member 55 to which the tool 52 is attached. The surgeon is able to rotate the holder about axis 172 without changing the ultimate target of the tool. Thus, rotation can be used to find an insertion path 170 that avoids grid elements 180 of the paddles.

Figure 14:
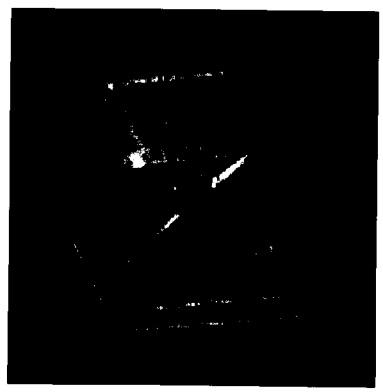
FIG. 14 is a perspective view (photograph) of the MRI reference marker.
Figure 15:
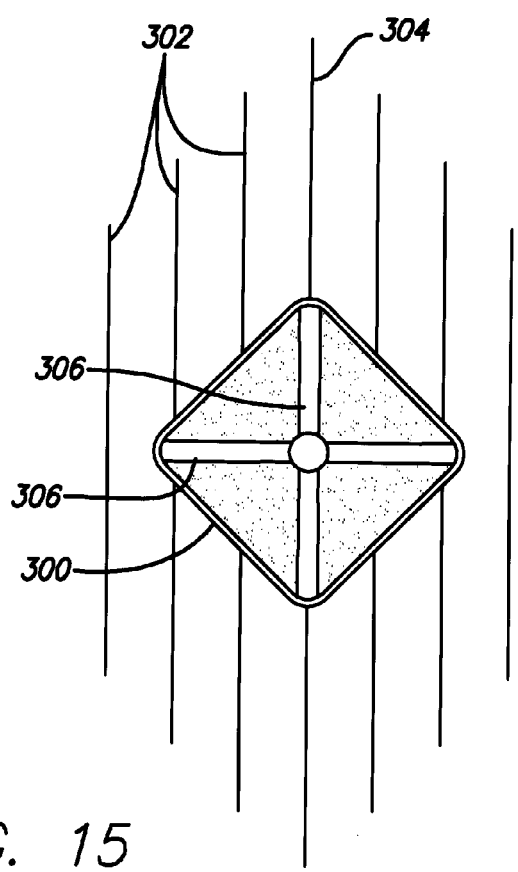
FIG. 15 is a cross-sectional view of the MRI reference marker.
Figure 13:
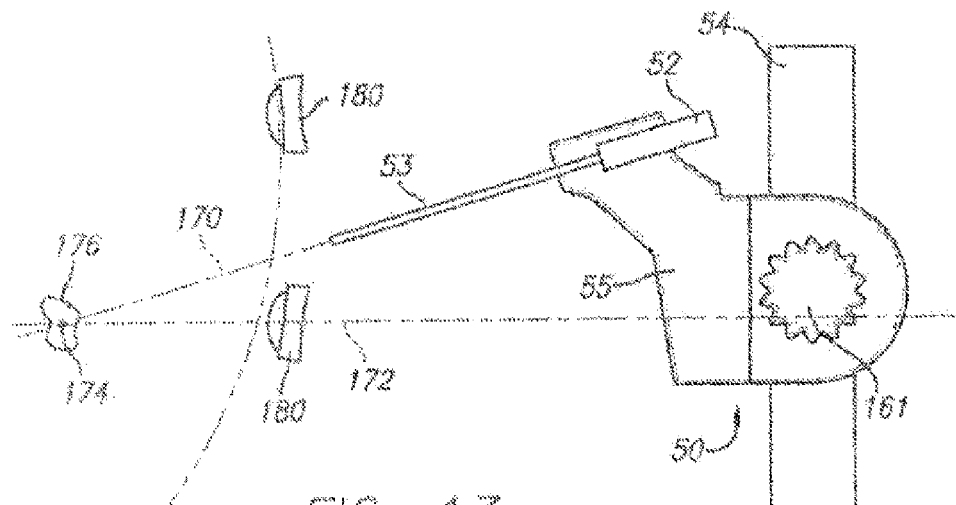
Figure 14:
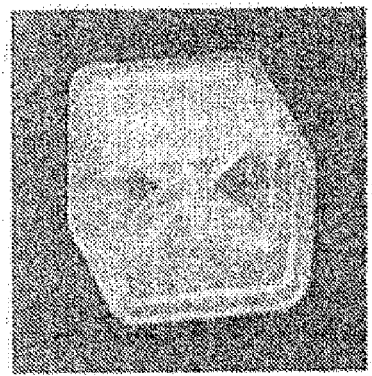
Figure 15:
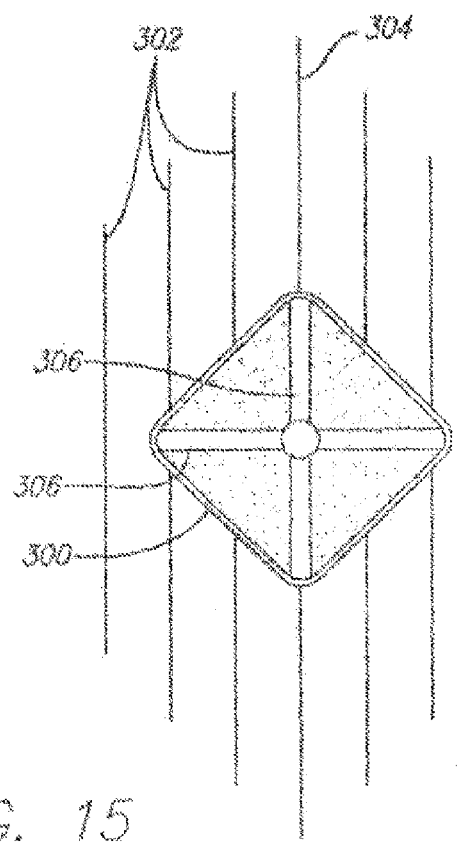

In operation, a series of MRI images are taken with a reference marker installed in the tool holder. The reference marker 300 preferably has a 3-dimensional cross hair configuration, as shown in FIGS. 14 and 15. The interior of the cube is filled with a liquid that shows up in the MRI image, and the polymer rods 306 extending through the cube in three orthogonal directions remain transparent in the image. It is not necessary that exactly the crosshair configuration shown be used, so long as the reference marker has a shape that permits its location to be determined from the images (preferably its X, Y, and Z location from one reference marker). Other shapes than cross hairs can accomplish that objective. Also, the arrangement in which the surrounding material is visible and the marking elements are transparent could be reversed, so that the marking elements (the cross hairs in the embodiment shown) could be made visible in the MRI image (e.g., by filling hollow rods with an MRI-visible material).

A preferred MRI visible material for use in constructing the reference marker is a hydrogel (superabsorbent) material, as it tends to expand and fill all cavities. But any of a wide variety of MRI-visible materials can also be used.

Preferably, the intersecting rods (or other elements) forming the reference marker are sized and positioned so that their intersection is visible on a single image slice and so that the elements appear in a plurality of adjacent slices. Having the intersection appear in a single slice improves accuracy. Having the elements appear in a plurality of adjacent slices makes it easier for the person observing the MRI slices to find the slice in which the intersection appears, as if it only appeared in a single slice it could be missed during review.

It is also preferable that the reference marker be shaped so that the MRI visible area grows in size from image slice to image slice as one approaches the image slice containing the intersection. This increases the likelihood that the reference marker will be seen in the image. If a cube shaped member 300 (FIG. 15) is used, this can be achieved by orienting the cube 300 so that a diagonal is parallel to the plane of the image slices 302, 304. In this orientation, the cross-section of the cube (which is what is visible, as it is filled with MRI-visible material) appearing in each slice 302 grows in size as one approaches the slice 304 containing the intersection.

The thickness of the intersecting rods (or other elements) should be fairly narrow for accuracy reasons. Preferably, the rods have a diameter on the order of the voxel size of the image (a voxel representing the three-dimensional volumetric granularity of the MRI system). If the rod thickness is much less than a voxel, it will not be seen, whereas if it is much greater, accuracy will be lost. For example, with a voxel size in the range of 1.0 to 2.0 mm, the rod thickness would preferably also be about 1.0 to 2.0 mm.

Software is used to permit an operator to locate the reference marker and the target (e.g., lesion). Straightforward mathematical operations are then performed to determine how much X, Y, and Z translation, and in which direction of translation, the tool holder needs to be moved so that the surgical tool will access the target upon insertion. A read out of the amount and direction of translation can be provided, and the operator can then adjust the tool holder's position until the outputs of the optical encoding sensors produce the specified translation. This can be facilitated by providing for zeroing of the displays prior to movement of the holder, so that all that is necessary is for the operator to move the holder until the displays read out the X, Y, and Z translations specified by the imaging software.

Once the holder has been moved to the correct location, the surgeon rotates the tool holder to find an insertion path that avoids the grid elements of the paddle or other obstruction, and initiates the surgical procedure. One option is to repeat the MRI imaging with the surgical tool inserted, and in that way confirm that the tool hit the anatomical target.

Other embodiments of the invention are within the following claims, and additional features described above and in the drawings form part of the invention and may be made the subject of claims.

What is claimed is:

1. A patient support table for breast MRI systems, the table comprising:
   a base configured to slide into and out of the bore of an MRI system;
   a patient support member attached to the base and having a top surface shaped to support a patient in a prone position;
   two breast openings in the patient support member, the breast openings being sized and positioned to permit the patient's breasts to extend downward beneath the patient support member;
   at least a pair of breast immobilization paddles, one on each side of a breast opening, the immobilization paddles comprising a grid of breast contact elements that contact the breast while providing a plurality of openings through which a surgical tool may be inserted into the breast; and
   the paddles having a convex curvature along the Z direction (head to toe) so that the breast contacting surface of each paddle is further from the Y-axis center line of the breast opening midway along the Z extent of the paddle than at the Z extremities of the paddle,
   wherein the convex curvature is greatest at the edge of the paddles corresponding to the base of the breasts at the chest wall,
   wherein the convex curvature at the edge corresponding to the base of the breast has a radius of curvature of at least 50 mm.

2. The patient support table of claim 1 wherein the convex curvature is progressively less at locations on the paddle further from the edge corresponding to the base of the breasts at the chest wall.

3. The patient support table of claim 2 wherein the paddles are substantially flat without curvature at the edge opposite the edge with curvature.

4. The patient support table of claim 1, 2, or 3 wherein the radius of curvature is at least 100 mm.

5. A patient support table for breast MRI systems, the table comprising:
   a base configured to slide into and out of the bore of an MRI system;

a patient support member attached to the base and having a top surface shaped to support a patient in a prone position;

two breast openings in the patient support member, the breast openings being sized and positioned to permit the patient's breasts to extend downward beneath the patient support member, at least a pair of breast immobilization paddles, one on each side of a breast opening, the immobilization paddles comprising a grid of breast contact elements that contact the breast while providing a plurality of openings through which a surgical tool may be inserted into the breast, and the paddles having a convex curvature along the Z direction (head to toe) so that the breast contacting surface of each paddle is further from the Y-axis center line of the breast opening midway along the Z extent of the paddle than at the Z extremities of the paddle, wherein the paddles are further shaped so that at the paddle edge closest to the breast opening, and to the chest when a breast is immobilized by the paddles, the paddles are flared outwardly with a radius of curvature greater than about 10 mm.

6. The patient support table of claim 5 wherein the convex curvature is greatest at the edge of the paddles corresponding to the base of the breasts at the chest wall.

7. The patient support table of claim 6 wherein the convex curvature is progressively less at locations on the paddle further from the edge corresponding to the base of the breasts at the chest wall.

8. The patient support table of claim 7 wherein the paddles are substantially flat without curvature at the edge opposite the edge with curvature.

9. The patient support table of claim 5 wherein the paddles are flared outwardly with a radius of curvature greater than about 15 mm.

* * * * *

UNITED STATES PATENT AND TRADEMARK OFFICE
CERTIFICATE OF CORRECTION

| | | |
|---|---|---|
| PATENT NO. | : 7,171,256 B1 | Page 1 of 2 |
| APPLICATION NO. | : 10/302734 | |
| DATED | : January 30, 2007 | |
| INVENTOR(S) | : David Graessle et al. | |

It is certified that error appears in the above-identified patent and that said Letters Patent is hereby corrected as shown below:

Title page, (75) Inventors, "Gunther Becht, Somerville, MA (US)" should be -- Gunther Becht, Heimstetten bei Munchen (DE) --.

Title page 2, OTHER PUBLICATIONS, at the "Fischer et al." reference, line 3, after "9", delete the comma.

Drawings, please replace sheet 11 of 11 with the attached replacement sheet.

Col. 1, line 38, "IT" should be -- it --.

Col. 4, line 61, "grater" should be -- greater --.

Signed and Sealed this

Thirteenth Day of January, 2009

JON W. DUDAS
*Director of the United States Patent and Trademark Office*